United States Patent [19]

Sumner, Jr. et al.

[11] Patent Number: 5,068,460
[45] Date of Patent: Nov. 26, 1991

[54] PROCESS FOR PREPARATION OF RESORCINOL

[75] Inventors: Charles E. Sumner, Jr.; Brenda J. Hitch, both of Kingsport; Bobby L. Bernard, Rogersville, all of Tenn.

[73] Assignee: Eastman Kodak Company, Rochester, N.Y.

[21] Appl. No.: 623,003

[22] Filed: Dec. 6, 1990

Related U.S. Application Data

[63] Continuation-in-part of Ser. No. 509,122, Apr. 16, 1990, abandoned.

[51] Int. Cl.$^5$ .............................................. C07C 41/01
[52] U.S. Cl. ................................................... 568/648
[58] Field of Search ................ 568/648, 649, 650, 651

[56] References Cited

U.S. PATENT DOCUMENTS 2,766,292 10/1956 Monson et al. ..................... 260/615

*Primary Examiner*—Howard T. Mars
*Assistant Examiner*—Margaret Argio
*Attorney, Agent, or Firm*—Charles R. Martin; William P. Heath, Jr.

[57] ABSTRACT

A process for preparation of resorcinol bis(hydroxyethyl)ether by first contacting resorcinol with ethylene carbonate and an alkali metal carbonate and then adding a solution of water and an alkali metal hydroxide and then recovering the resorcinol bis(hydroxyethyl)ether by crystallization.

2 Claims, No Drawings

PROCESS FOR PREPARATION OF RESORCINOL

This application is a continuation-in-part of Ser. No. 07/509,122 filed Apr. 16, 1990, now abandoned.

This invention relates to a process for preparation of resorcinol bis(hydroxyethyl)ether by first contacting resorcinol with ethylene carbonate and an alkali metal carbonate and then adding a solution of water and an alkali metal hydroxide and then recovering the resorcinol bis(hydroxyethyl)ether by crystallization.

As disclosed in U.S. Pat. No. 2,766,292 phenols are known to react with ethylene carbonate in the presence of an alkali carbonate catalyst to produce the corresponding hydroxyethyl ether. When this procedure is applied to dihydroxybenzenes preparation of the bis(2-hydroxyethyl)ether is accompanied by several by-products including hydroxyethoxyphenols, (2-hydroxyethyl)oxyethyl phenyl ethers, and polymeric materials which manifests themselves as an oil in the product. These by-products render the bis(2-hydroxyethyl)ether compounds unsuitable for many applications. Furthermore, the oil-like polymer by-product inhibits the crystallization of the bis(2-hydroxyethyl)ether thus complicating its isolation and purification.

The process of this invention is an improvement over the prior art because in this process of this invention a higher yield and purity is obtained by conducting the additional step of adding a solution of water and sodium hydroxide to the reaction products of the reaction of resorcinol and ethylene carbonate prior to crystallization to recover the resorcinol bis(hydroxyethyl)ether.

The process of the invention is composed of three steps. The first step is contacting resorcinol and ethylene carbonate and an alkali metal carbonate. Then a solution of water and an alkali metal hydroxide which is at least 0.6 molar is added to the reaction products of the first step. Then the resorcinol bis(hydroxyethyl)ether is recovered by crystallization.

In the first step of the process resorcinol reacts with ethylene carbonate and an alkali metal carbonate to produce resorcinol bis(hydroxyethyl)ether and a variety of unwanted by-products according to the following reaction

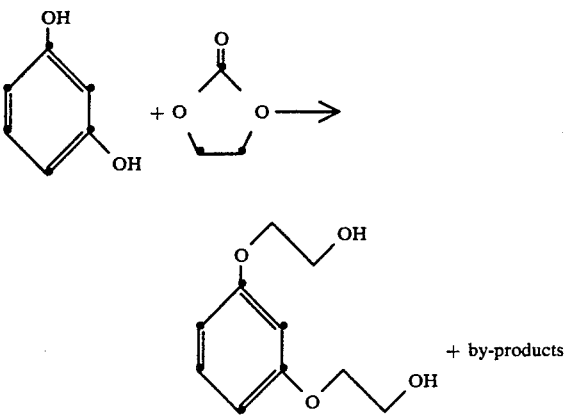

The reaction is conducted for a sufficient length of time and at a sufficient temperature for the resorcinol bis(hydroxyethyl)ether to form in good yield. A temperature in the range of 130°–150° C. is particularly satisfactory. Typically the reaction time is about 1 to 10 hours, preferably 4 to 6 hours.

The reaction can be conducted commercially in general purpose stirred reactors.

The alkali metal in this alkali metal carbonate can be any alkali metal but potassium is preferred.

In the second step of the process a solution of water and an alkali metal hydroxide is added to the reaction products of the first step composed of resorcinol bis(hydroxyethyl)ether and various unwanted by-products. The alkali metal in the alkali metal hydroxide can be lithium, sodium, or potassium but sodium is preferred. The solution is at least 0.6 molar, preferably at least 0.9 molar. The concentration of the caustic solution can be as low as 2% and as high as 20%. A concentration of 3–8% is optimal, and 4% is preferred. The rate at which the solution is added is such that the temperature of the mixture is maintained at 50° to 90° C.

The second step can be conducted commercially by adding the caustic solution to the same standard stirred reactor used to conduct the first step.

The third step of the process is recovery of the resorcinol bis(hydroxyethyl)ether by crystallization. The resorcinol bis(hydroxyethyl)ether is recovered from the result of adding the solution of water and alkali metal hydroxide to the reaction products of the first step by conventional crystallization technique well known in the art. For example the crystallization can be accomplished by simply cooling the mixture until the resorcinol bis(hydroxyethyl)ether precipitates, and recover the precipitate.

The resorcinol bis(hydroxyethyl)ether prepared by the process of this invention is useful as a polyurethane chain extender and as an intermediate for phenylenedioxydiacetic acid derivatives which are known to impart enhanced gas barrier properties to polyesters.

EXAMPLE 1

This example illustrates the prior art where there is no solution of water and an alkali metal hydroxide added to the reaction products of step one prior to recovery by crystallization.

To a 12 L flask equipped with a stirrer, reflux condenser, $N_2$ inlet, addition funnel, and heating mantle was added ethylene carbonate (1,936 g; 22 mole), resorcinol (1,101 g; 10 mole) and potassium carbonate (10 g; 0.07 mole). The apparatus was purged with $N_2$ until the oxygen content was measured to be less than 1%. The mixture was stirred and gradually heated to 140° C. When the temperature reached 40° C., the stirring speed was increased to 100 rpm. At 125° C., the mixture began to evolve $CO_2$. The mixture was heated at 140° C. for 6 hours, after which time it was cooled to 90° C., and 4 L of water was added at a rate of 44 mL/min. while the temperature was maintained above 50° C. The resulting mixture was stirred at 100 rpm and cooled to 50° C. Resorcinol bis(hydroxyethyl)ether (2 g) was added as seed crystals and the mixture was cooled to 18° C. at a rate of 5°/min. and held at this temperature for 1 hour. The product was collected by filtration, washed twice with 1 L portions of water, and dried in a vacuum oven at 50° C. The yield was 1,366 g (69%) and contained an oily material which separated upon dissolving the material in warm water.

EXAMPLE 2

This example illustrates practice of the invention.

To a 1 L 3-neck flask equipped with a mechanical stirrer, heating mantle, reflux condenser, thermocouple well, and argon atmosphere, was added resorcinol (110 g; 1 mole), ethylene carbonate (194 g; 2.2 mole), and potassium carbonate (1 g; 7 "mmole"). The resulting mixture was heated at 140° C. for 6 hours during which time $CO_2$ was evolved. The mixture was cooled to 90° C. and 400 mL of 4% NaOH solution was added over a 10 min. period while the temperature of the mixture was allowed to decrease to 53° C. The mixture was allowed to slowly cool to 20° C. to precipitate the resorcinol bis(hydroxyethyl)ether, and the resorcinol bis(hydroxyethyl)ether was collected by filtration, washed with 50 mL of water, and dried for 12 h in a vacuum oven. The dry product weighed 186 g (94%).

EXAMPLE 3-7

The invention was practiced by repeating Example 1 except 4 L of a sodium hydroxide solution was used in place of the 4 L of water. The presence of an oil-like by-product and the yield of resorcinol bis(hydroxyethyl)ether as a function of the concentration of NaOH used in the solution is summarized below.

| Example No. | NaOH | Yield | Oil-like By-product Present |
| --- | --- | --- | --- |
| 3 | 0.25M | 80.7% | yes |
| 4 | 0.38M | 83.3% | yes |
| 5 | 0.50M | 86.2% | yes |
| 6 | 0.63M | 93.0% | yes |
| 7 | 1.00M | 94.4% | no |

We claim:
1. A process for preparation of resorcinol bis(hydroxyethyl)ether comprising
   (A) contacting at a temperature in the range of 130 degrees to 150 degrees C. resorcinol and ethylene carbonate and an alkali metal carbonate,
   (B) adding a solution of water and an alkali metal hydroxide which is at least 0.6 molar, and
   (C) recovering the resorcinol bis(hydroxyethyl)ether by crystallization.
2. A process for preparation of resorcinol bis(hydroxyethyl)ether comprising
   (A) contacting at a temperature in the range of 130 degrees to 150 degrees C. resorcinol and ethylene carbonate and potassium carbonate,
   (B) adding a solution of water and sodium hydroxide which is at least 0.9 molar, and
   (C) recovering the resorcinol bis(hydroxyethyl)ether by crystallization.

* * * * *